United States Patent
Rusin

(10) Patent No.: US 6,412,491 B1
(45) Date of Patent: Jul. 2, 2002

(54) EXAMINATION DEVICE AND METHOD

(76) Inventor: James D. Rusin, 3512 Run River Dr., Anoka, MN (US) 55303-1109

(*) Notice: Subject to any disclaimer, the term of this patent is extended or adjusted under 35 U.S.C. 154(b) by 0 days.

(21) Appl. No.: 09/526,244

(22) Filed: Mar. 15, 2000

(51) Int. Cl.⁷ .............................................. A61B 19/00
(52) U.S. Cl. ..................................... 128/897; 128/898
(58) Field of Search .............................. 600/300, 549, 600/587, 407; 128/898; 434/267

(56) References Cited

U.S. PATENT DOCUMENTS

| | | | | | |
|---|---|---|---|---|---|
| 4,524,778 A | * | 6/1985 | Brown, Jr. et al. | ......... | 600/549 |
| 4,737,109 A | * | 4/1988 | Abramson | ................ | 434/267 |
| 4,867,686 A | * | 9/1989 | Goldstein | ................ | 434/267 |
| 4,873,982 A | * | 10/1989 | Morrison | ................ | 600/300 |
| 5,894,844 A | * | 4/1999 | Rohrberg | ................ | 128/898 |
| 5,916,180 A | * | 6/1999 | Cundari et al. | ............. | 600/587 |
| 6,091,981 A | * | 7/2000 | Cundari et al. | ............. | 600/407 |

* cited by examiner

Primary Examiner—Eric F. Winakur
Assistant Examiner—Nikita R. Veniaminov
(74) Attorney, Agent, or Firm—Beck & Tysver, P.L.L.C.

(57) ABSTRACT

A non-elastic conformal translucent device is applied to the chest and breast of a patient to facilitate tissue examination.

19 Claims, 2 Drawing Sheets

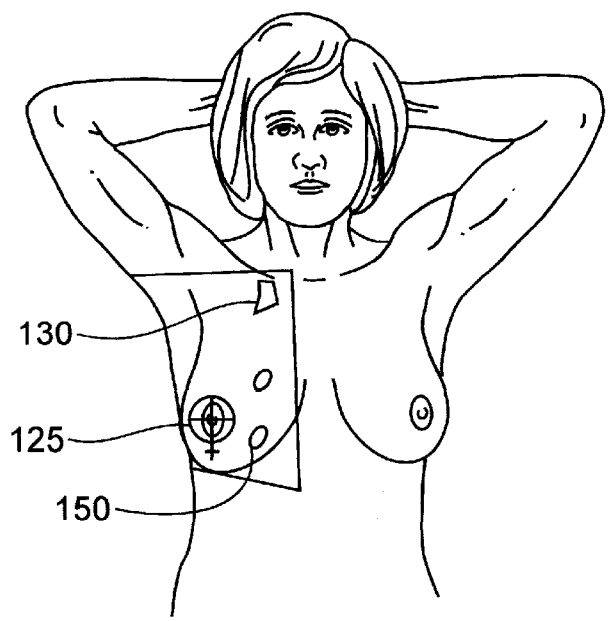
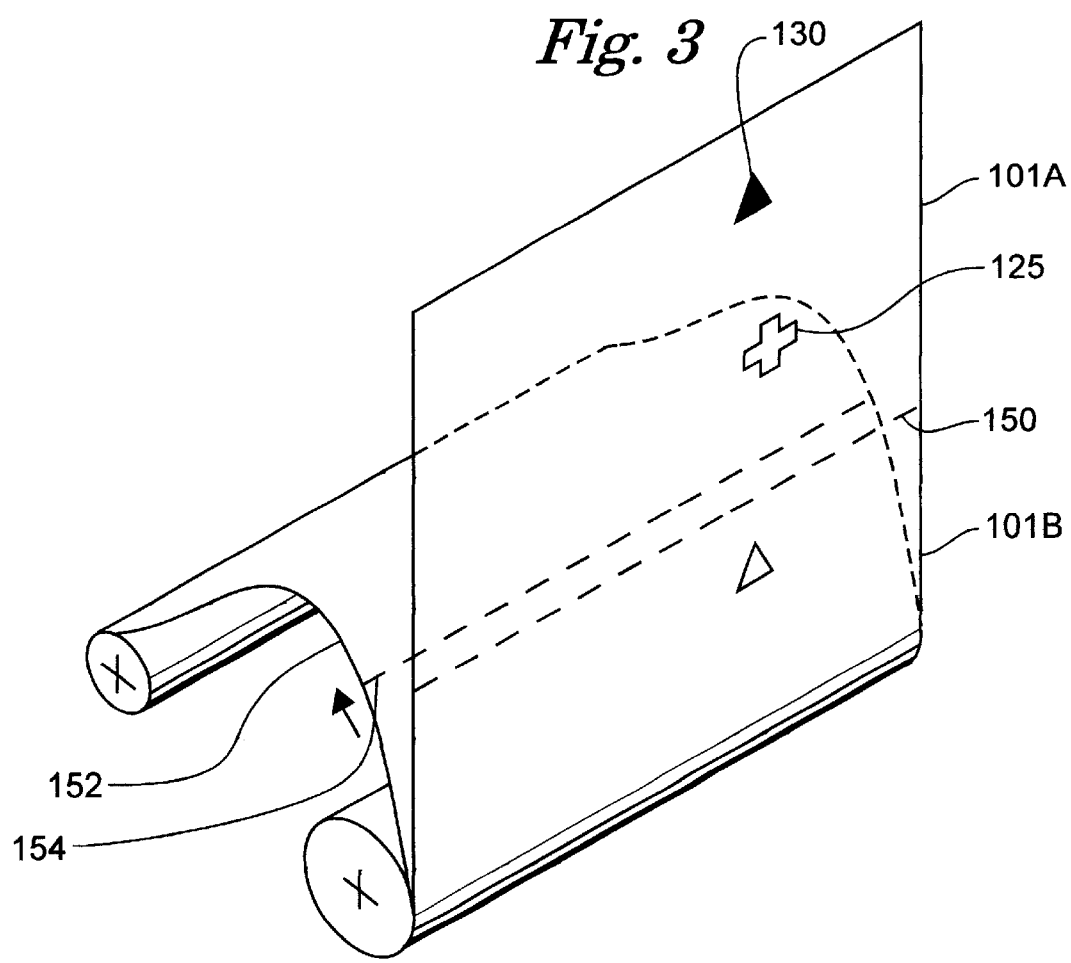

EXAMINATION DEVICE AND METHOD

FIELD OF THE INVENTION

The present invention relates generally to the field of medicine and more particularly to a device and method for conducting a breast examination.

BACKGROUND OF THE INVENTION

Tactile physical examination of the breast is an important screen for breast cancer. Both physician examination and self examination are widely practiced. The palpation or detection of "lumps" in the breast is the principle objective of a breast examination.

Early detection of "lumps" is very desirable but difficult due to the relatively small size of lumps and their location within a mass of otherwise healthy tissue. As a consequence, and in many instances, a single lump will be evaluated by several people to confirm detection.

The classic tactile examination involves sliding fingers over the skin to detect lumps. The friction may cause patient discomfort and the friction always reduces the sensitivity of the fingers. Consequently the examiner is frequently required to pause and examine the small portion of the tissue beneath their fingers, lift their fingers from the tissue, reapply them to an adjacent portion of the tissue, and repeat the palpation maneuver. This extended series of motions is continued until the entire area of concern has been examined. One disadvantage with this intermittent method of examination is that lumps may be missed or passed over during the examination due to the repeated lifting and repositioning of the examiner's hands.

Another problem with direct contact is the tendency for the tissue under examination to be move when pressure of the examiner's hand is applied to the tissue. This is particularly problematic for thick and soft tissues. The movement of tissue has at least two undesirable effects. First, portions of the tissue may escape tactile examination. Second, after a potentially pathological feature, such as a lump, is detected by tactile examination, the location of such feature is difficult to describe with accuracy. Consequently, subsequent search for the feature is difficult.

Another significant drawback with tactile examinations involves the embarrassment that some patients experience when a physician conducts such extensive exams. Embarrassment or modesty can reduce the frequency of such examinations reducing the early detection of cancer. These embarrassment and modesty issues may also complicate or hinder the actual examination, thereby undercutting the effectiveness of such procedures.

Various examination garments have been created to address these problems. For example, U.S. Pat. Reissue No. 34,353 discloses a pad which includes a sealed enclosure made of an elastic material such as latex rubber. The pad contains a liquid lubricant inside the enclosure. During a tactile examination, the top wall of the enclosure moves with the hand of the examiner while the bottom wall remains stationary relative to the object being examined. Other patented arrangements have addressed the issues of associated with tactile examination. U.S. Pat. No. 3,154,789 discloses a disposable examination garment comprising a vest-type article having individual flaps for selectively revealing one breast at a time for examination. U.S. Pat. No. 4,873,982 discloses yet another examination garment for conducting tactile breast examinations. The garment comprises a "tube-top" type article having a form-fitting elastic inner ply and a loose-fitting elastic outer ply. The garment covers the breasts during the tactile examination, thereby aiding modesty. The elastic inner and outer plies are designed to have a reduced coefficient of friction to allow the examiner's fingers to slide more readily while traversing the breast. A significant drawback exists, however, in that the fabric is thick and thus diminishes the tactile sensitivity of the examiner.

The present invention is directed at overcoming the problems set forth above.

SUMMARY OF THE INVENTION

The present invention is an examination device which can be used to facilitate physical examination of the breast. The invention is disclosed in the context of a breast examination but may be used in other applications as well. The device includes a drape which can be applied to the body. It has a smooth "reduced friction" surface on one side and a complimentary surface that clings to exposed skin. Fiducial markers on the device are provided to orient the device on the body. The device accepts indicia or markers that can be used to identify and to relocate "suspected" lumps.

BRIEF DESCRIPTION OF THE DRAWINGS

The advantages of the invention will become apparent upon reading the following detailed description and upon reference to the drawings which show an illustrative embodiment of the device, in which:

FIG. 2 shows one aspect of an illustrative method of the present invention;

FIG. 3 shows a plurality of examination devices dispensed in a roll.

DETAILED DESCRIPTION OF THE PREFERRED EMBODIMENT

Figure 1:
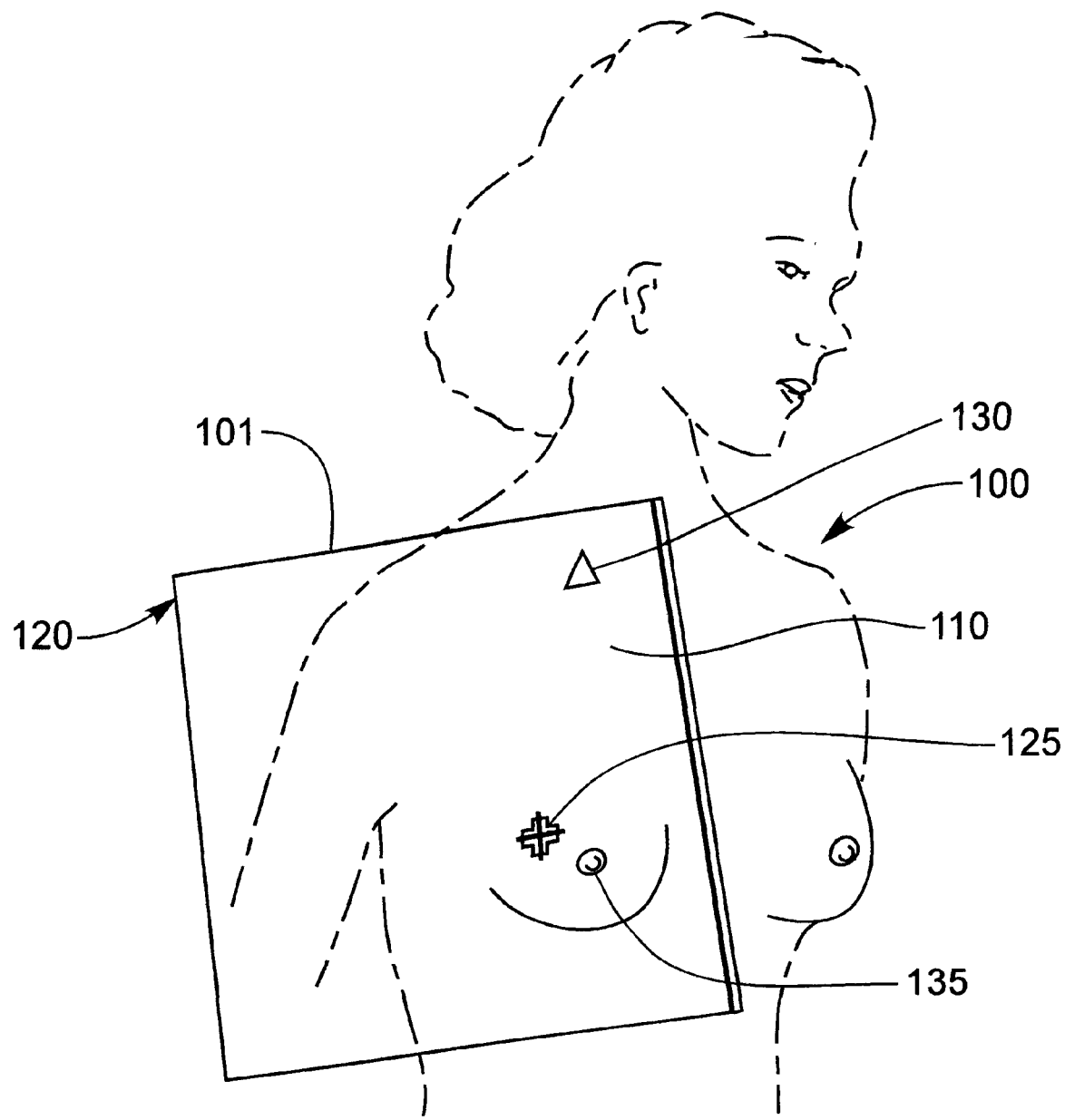
FIG. 1 shows a device embodying the present invention.

FIG. 1 shows an illustrative embodiment of the present invention positioned near but not on a patient 100. The device 101 is depicted as a transparent film for purposes of illustration. Translucent or partially opaque materials are contemplated within the scope of the invention and may be preferable. In general polymeric films will be the best material to create the device 101. Conventional surface treatments can be used to make one side "slippery" and the other side "clingy". The device 101 has a "top" surface 110 facing toward the observer while the "bottom" surface 120 is closest to the skin of the patient 100. In practice the patient or her physician will place the fiducal mark 125 over the patient nipple 135. The orientation mark 130 near the top of the device 101 is shown as an arrow pointed upwardly toward the head of the patient 100. Once the device is appropriately positioned it is pressed onto the patient and allowed to attach or cling to the patient.

FIG. 2 shows the device 101 placed on the patient 100. In general the bottom surface 120 has a coefficient of friction that is higher than the coefficient of friction of the top surface 110. The difference in the frictional properties of the two surfaces ensures that when the device 101 is draped over a portion of the patient's body 100 during a tactile examination the bottom surface 120 will remain in contact with the patient and will not slide relative to the patient's skin while the examiners hand slides over the top surface 110 of the device 101.

The bottom surface 120 may optionally have a stronger tendency to cling to human skin than the top surface 110.

The ability of the bottom surface 120 to cling to human skin facilitates placement and stabilization of the breast region under examination. Such stabilization has the added advantage that when the device 101 is reused and reapplied for later re-identification of the points of interest. The device more nearly resumes its same location of the body.

As seen in the drawing of FIG. 2, the device 101 includes a fiducial or location marker 130 that indicates the orientation of the device 101. The location marker 130 may be of any indicia sufficient to aid the identification of a point on the device 101. For example, the location marker 130 may simply be a dot, a circle or a cross marking a point near or at the center or an edge of the device 101.

The direction or location marker 130 may be of any indicia sufficient to aid the orientation of the film 100 along a chosen direction. For example, the marker 130 may simply be an arrow printed on the sheet pointing in a given direction, such as upward toward the head. It is desirable to use one device for both the right and left breast so it may be useful to make the position of the marker asymmetric to aid in orienting the device. The fiducal mark 125 may be either an "X" or cross to allow alignment with the nipple or other anatomic reference.

The device embodying the present invention may also include a marker 150 attachable to the device 101 for identification of a location of interest on the portion of the human body under examination. The attachable marker 150 may simply be a round adhesive label which may be applied to identify the location of a lump. It is highly desired that the attachment be permanent so that the marker cannot be repositioned without destroying the device 101. Marking pens may also be used to fulfill this permanent marking requirement.

As illustrated in FIGS. 1 and 2, the method of the present invention includes using a device 101 with different contact properties for the top and bottom surfaces in the tactile examination of a portion of the human body such as a breast. In an illustrative method of the present invention, the examiner (e.g. a physician conducting a tactile breast examination on a patient or a patient conducting self breast examination) places a device 101 over the portion of the human body, such as a breast, for examination. Next the examiner then slides the examining hand across the top surface 110 of the device 101 while applying pressure to the top surface 110 of the film 100 with the examining hand so that the device 101 does not slide relative to the skin of the portion of the human body to be examined.

When a lump of interest is found on the patient's body it is identified through tactile examination, and the examiner may mark the point of interest on the device 101 with marker 150. For example, if the examiner feels a lump in the breast and concludes that the lump should be further investigated a radiologist, the examiner may place a small adhesive label on the device 101 over the point where the lump was felt. A conventional felt marking pen may be used as well. In either event the patient may then take the marked device 101 to the radiologist, who then repositions the device 101 on the patient's breast using the location marker 140 and the fiducial marker 125 to position and orient the sheet exactly as it had been positioned and oriented during the initial exam. In this manner the marker positioning and orientation procedures as above. The position of the adhesive label now indicates the approximate location of the lump. The efficiency of re-identification of the lump is thus greatly enhanced over many conventional methods. The device may be removed from the patient and reapplied at a later time to facilitate a further examination. The device is not elastic and yet it is sufficiently conformal to allow the reapplication process to reposition the markers in the "same" location as the original fitting. This lack of elasticity also functions to stabilize the beast as the device is sufficiently large (nominal 12×16) to overlap the chest and breast.

It is preferred to apply the device to one breast at a time as this enhances the stabilizing effect.

FIG. 3 shows a preferred technique for dispensing the devices 101. Each device is attached to a companion device by a serrated edge 150 seen between device 101A and 101B. A tissue paper release liner 152 maybe provided to facilitate dispensing a device 101a from the "roll". The tissue paper may also have serration or it may be precut so that a piece of tissue is available to wrap the device 101 after use. This expedient prevents wadding up of the device after removal.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternative falling within the spirit and scope of the invention as defined by the appended claims.

What is claimed is:

1. A method for tactile examination of a single breast of a human body, comprising the steps of:

providing a single layer planar film device having a top surface and a bottom surface, said top surface having a first coefficient of friction; said bottom surface having a second coefficient of friction that is higher than the first coefficient of friction, said second coefficient of friction sufficient to retain said film device in contact said breast such that there is no relative movement between said film device and said breast;

placing the film device over the portion of the breast so that the bottom surface of the film is in contact with the skin of the portion of the human breast to be examined; and sliding the examining hand across the top surface of the film device while applying a pressure to the top surface of the film device with the examining hand so that the film does not slide relative to the skin of the portion of the human breast to be examined.

2. The method of claim 1, further comprising the steps of:

providing on the film device a fiducial marker indicative of a specific location on the device;

providing on the device a direction marker indicative of a direction relative to the single breast;

matching the position of the fiducial marker to the position of a predetermined location on the portion of the breast; and aligning the direction marker with a predetermined direction relative to the portion of the breast.

3. The method of claim 2, further comprising the step of:

providing on the film device an examination marker indicative of the location of a point of interest on the portion of the breast.

4. The method of claim 3, wherein the step of providing a marking includes attaching to the device an adhesive label indicative location of a point of interest on the portion of the breast.

5. The method of claim 3 wherein said examination marker is a mark applied to the film device with a hand held marker pen.

6. The method of claim 2, wherein the tactile examination of a portion of a human breast includes:
- tactile examination of a single breast of supine patient, the step of matching includes positioning the location indicated by the fiducial marker substantially on top of the nipple, and,
- the step of aligning includes aligning the direction indicated by the direction marker substantially cephalad.

7. The method of claim 6, further comprising:
- providing clinging contact between the film device and the skin of the breast and surrounding area to stabilize the breast of the supine patient.

8. A method for tactile examination of a portion of a single human breast, comprising the steps of:
- providing a sheet of transparent polymeric film having a top surface, and a bottom surface, and a periphery, said bottom surface having a stronger tendency to cling to human skin than the top surface;
- placing the film over the portion of the human breast so that the bottom surface of the film is in contact with the skin of the portion of the human breast to be examined; and
- sliding the examining hand across the top surface of the film while apply a pressure to the top surface of the film with the examining hand such that the film does not slide relative to the skin of the portion of the human breast to be examined.

9. The method of claim 8, further comprising the steps of:
- providing on the sheet of film a fiducial marker indicative of a location on the film;
- providing on the sheet of film a direction marker indicative of a direction relative to the film;
- matching the position of the fiducial marker to the position of a predetermined location on the portion of the human breast; and
- aligning the direction marker with a predetermined direction relative to the portion of the human breast.

10. The method of claim 9, further comprising the step of:
- providing on the sheet of film an examination marking indicative of the location of a point of interest on the portion of the human breast.

11. The method of claim 10, wherein the step of providing an examination marking includes:
- attaching to the film an adhesive label indicative location of a point of interest on the portion of the human breast.

12. The method of claim 9, wherein:
- the tactile examination of a portion of a human breast includes tactile examination of a breast;
- the step of matching includes positioning the location indicated by the fiducial marker substantially on top of the nipple;
- the step of aligning includes aligning the indicated by the direction marker substantially along the length of the human breast towards the head.

13. The method of claim 12, further comprising:
- providing clinging contact between the film and the skin of the breast and surrounding area to stabilize the breast.

14. The method of claim 13, further comprising:
- stretching the film prior to providing the clinging contact so that the film clings to the skin of the human breast under tension so as to reduce tissue movement in the portion to be examined.

15. A device for tactile physical examination of a single human breast, comprising:
- a film having a top surface and a bottom surface, said top surface having a first coefficient of friction, said bottom surface having a second coefficient of friction that is higher than the first coefficient of friction;
- a fiducial marker on the film indicative of a specific location on the film; and
- a direction marker on the film indicative of a direction relative to the sheet of film on the human breast.

16. The device of claim 15, further comprising:
- an examination marker attachable to the film by a user for marking the location of a point of interest on the portion of the human breast under examination.

17. The device of claim 16, wherein the attachable examination marker comprises an adhesive label.

18. The device of claim 15, wherein the bottom surface has a stronger tendency to cling to human skin than the top surface.

19. The device of claim 15, wherein the top surface has no tendency to cling to human skin.

* * * * *